US009977005B2

(12) United States Patent
Carteau et al.

(10) Patent No.: US 9,977,005 B2
(45) Date of Patent: May 22, 2018

(54) GAS SAMPLING DEVICE AND FILLING STATION COMPRISING SUCH A DEVICE

(71) Applicant: L'Air Liquide, Societe Anonyme pour l'Etude et l'Exploitation des Procedes Georges Claude, Paris (FR)

(72) Inventors: David Carteau, Buc (FR); Patrick Mauvais, Auffargis (FR)

(73) Assignee: L'AIR LIQUIDE SOCIETE ANONYME POUR L'ETUDE ET L'EXPLOITATION DES PROCEDES GEORGES CLAUDE, Paris (FR)

( * ) Notice: Subject to any disclaimer, the term of this patent is extended or adjusted under 35 U.S.C. 154(b) by 114 days.

(21) Appl. No.: 15/021,169

(22) PCT Filed: Jul. 30, 2014

(86) PCT No.: PCT/FR2014/051982
§ 371 (c)(1),
(2) Date: Mar. 10, 2016

(87) PCT Pub. No.: WO2015/036669
PCT Pub. Date: Mar. 19, 2015

(65) Prior Publication Data
US 2016/0223510 A1 Aug. 4, 2016

(30) Foreign Application Priority Data
Sep. 12, 2013 (FR) ...................................... 13 58752

(51) Int. Cl.
*G01N 33/22* (2006.01)
*F17C 5/06* (2006.01)
(Continued)

(52) U.S. Cl.
CPC ............... *G01N 33/22* (2013.01); *F17C 5/06* (2013.01); *G01N 1/2035* (2013.01);
(Continued)

(58) Field of Classification Search
CPC .......... G01N 33/22; G01N 2001/2238; G01N 1/2035; G01N 2001/205; G01N 2001/105;
(Continued)

(56) References Cited

U.S. PATENT DOCUMENTS 5,101,671 A  4/1992 Elgas
5,116,330 A  5/1992 Spencer
(Continued)

FOREIGN PATENT DOCUMENTS

CN  101 418 908  4/2009

OTHER PUBLICATIONS

International Search Report, and Written Opinion for PCT/FR2014/051982, dated Oct. 31, 2014.
(Continued)

*Primary Examiner* — Peter Macchiarolo
*Assistant Examiner* — Anthony W Megna Fuentes
(74) *Attorney, Agent, or Firm* — Christopher J. Cronin

(57) ABSTRACT

The invention relates to a gas sampling device for a filling station for hydrogen tanks, said device comprising a circuit comprising a first upstream end provided with an inlet connector to a detachably connected to an outlet connector of a filling station, and two conduits respectively for sampling and filling connected in parallel to the inlet connector, the sampling conduit comprising a valve system, a first pressure reducing valve and a container for collecting a sample of gas expanded by said first pressure reducing valve, and the filling conduit comprising a downstream end
(Continued)

provided with a first outlet connector to a detachably connected to an inlet connector of a tank to be filled.

11 Claims, 1 Drawing Sheet

(51) Int. Cl.
    *G01N 1/20*     (2006.01)
    *G01N 1/22*     (2006.01)
    *G01N 1/10*     (2006.01)

(52) U.S. Cl.
    CPC .............. *F17C 2221/012* (2013.01); *F17C 2223/0123* (2013.01); *F17C 2223/036* (2013.01); *F17C 2250/00* (2013.01); *F17C 2270/0139* (2013.01); *G01N 2001/105* (2013.01); *G01N 2001/205* (2013.01); *G01N 2001/2238* (2013.01)

(58) Field of Classification Search
    CPC .............. F17C 5/06; F17C 2221/012; F17C 2223/0123; F17C 2250/00; F17C 2270/0139; F17C 2223/036
    See application file for complete search history.

(56) References Cited

U.S. PATENT DOCUMENTS

| | | | |
|---|---|---|---|
| 5,209,102 A | | 5/1993 | Wang et al. |
| 5,437,199 A | | 8/1995 | Kaplan |
| 6,827,101 B2 | * | 12/2004 | Tetreault ............ F02M 25/0809 137/565.23 |
| 2006/0172428 A1 | | 8/2006 | McDermott et al. |
| 2007/0157969 A1 | | 7/2007 | Gross |
| 2013/0008557 A1 | * | 1/2013 | Cohen ................. G05D 11/132 141/9 |

OTHER PUBLICATIONS

French Search Report and Written Opinion for FR 1 358 752, dated Jul. 8, 2014.

* cited by examiner

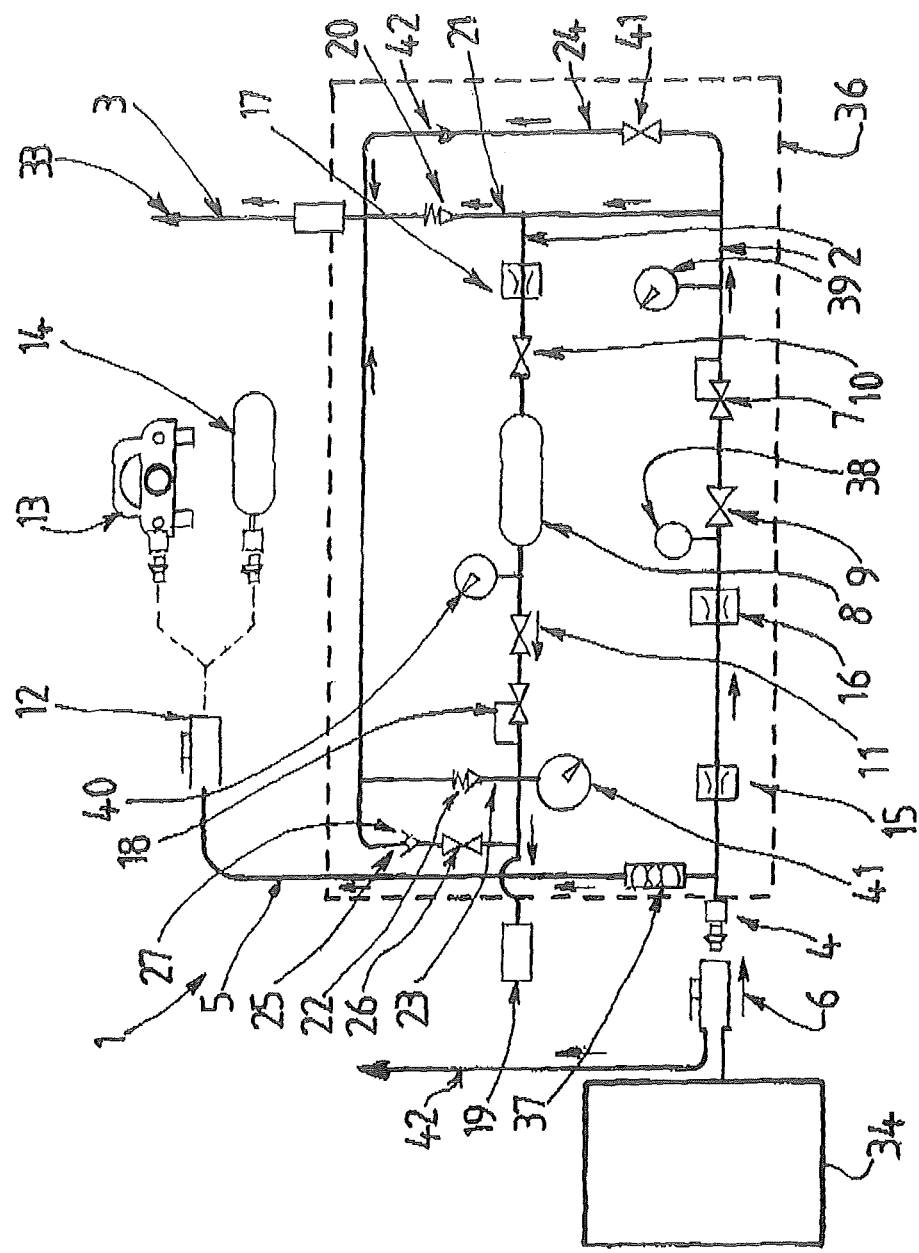

US 9,977,005 B2

GAS SAMPLING DEVICE AND FILLING STATION COMPRISING SUCH A DEVICE

CROSS-REFERENCE TO RELATED APPLICATIONS

This application is a § 371 of International PCT Application PCT/FR2014/051982, filed Jul. 30, 2014, which claims § 119(a) foreign priority to French patent application 1358752, filed Sep. 12, 2013.

BACKGROUND

Field of the Invention

The present invention relates to a gas sampling device and to a tank filling station comprising such a device.

Related Art

The impurities contained in hydrogen may adversely affect the operation of proton exchange membrane fuel cells (PEMFC) fitted to vehicles and other mobile applications. In order to optimize the performance and life thereof, the hydrogen supplied to the fuel cells needs to meet strict quality requirements which are published in international standards.

Most hydrogen is generally produced via industrial processes such as the steam reforming of natural gas (which is the most commonly used) or the gasification of coal. Hydrogen may also be produced by less conventional processes such as the gasification of biomass or the electrolysis of water.

Purification processes make it possible to generate hydrogen of very high purity (superior to 99.9% depending on circumstances) which may nevertheless still contain impurities the nature and concentration of which are directly dependent on the production process and also the production source (natural gas, coal, naphtha, biomass, water, etc.). Certain impurities (carbon monoxide CO, hydrogen sulfide $H_2S$, ammonia $NH_3$) have an irreversible, or reversible as the case may be, effect on the operation of proton exchange membrane fuel cells. Other impurities (carbon dioxide, oxygen, hydrocarbons, formaldehyde, etc.) have less of an effect on the operation of fuel cells.

All of the impurities are listed in standard ISO 14687-2 which defines the nature and concentration of the species that are to be analyzed.

In order to check the quality of the hydrogen using laboratory analysis techniques, samples of hydrogen need to be taken at the point of use, namely at the high-pressure (350 bar or 700 bar for example) gas outlet of the filling stations.

Most impurities are relatively difficult to analyze. The very low level of concentration desired (for example of the order of one ppb in the case of $H_2S$ and around 200 ppb in the case of CO) and the reactivity of certain species ($H_2S$, $NH_3$) with respect to certain materials call for a particularly demanding sampling technique.

The technical constraints associated with such analysis are numerous, and notably:
 the gas pressures and flow rates to be analyzed are high,
 there is a need to perform chemical passivation of the materials in order to limit the adsorption of contaminants,
 the equipment needs to exhibit a high degree of purity,
 the hardware used needs to be suited to the high pressure,
 the equipment needs to meet safety constraints ("ATEX" explosive atmosphere regulation) etc.

The ability to take a representative hydrogen sample without the risk of introducing a contaminant, even at a very low content (ppb=parts per billion), is therefore key because it needs to make it possible to evaluate the quality of the fuel supplied to the tanks being filled.

There is an ASTM standard regarding the sampling of hydrogen.

Document CN101418908A1 describes a hydrogen tank filling station incorporating a sampling device. The filling station comprises an outlet connector dedicated to the sampling and sampling gas upstream of the regulating members that regulate the flow supplied to the tank that is to be filled.

Such a device allows a gas sample to be taken at the same time as filling is being carried out but does not guarantee that the hydrogen sampled is under the conditions under which a vehicle is filled. In addition, this device entails the use of components compatible with a relatively high pressure and may be incompatible with the objective of purity of the gas.

This sampling principle also requires relatively complex or costly arrangements regarding the architecture of the filling station.

SUMMARY OF THE INVENTION

It is an object of the present invention to alleviate all or some of the abovementioned disadvantages of the prior art.

To this end, the sampling device according to the invention, in other respects in accordance with the generic definition given thereof in the above preamble, is essentially characterized in that it comprises a circuit comprising a first upstream end provided with an inlet connector intended to be connected removably to an outlet connector of a filling station and two pipes, these respectively being a sampling pipe and a filling pipe, which are connected in parallel to the inlet connector, the sampling pipe comprising a system of valves, a first pressure regulator and a container for collecting a sample of gas expanded by said first regulator, the filling pipe comprising a downstream end provided with a first outlet connector intended to be connected removably to an inlet connector of a tank that is to be filled.

Moreover, certain embodiments of the invention may have one or more of the following features:
 the sampling pipe comprises at least one calibrated orifice situated upstream of the first pressure regulator, namely between the inlet connector and the first pressure regulator,
 the sampling pipe comprises a calibrated orifice situated downstream of the first regulator, namely between the first regulator and the collecting container,
 the sampling pipe comprises a first and a second calibrated orifice which are arranged in series upstream of the first regulator, namely situated between the inlet connector and the first regulator, the first calibrated orifice having an orifice of dimensions greater than the dimensions of the orifice of the second calibrated orifice,
 the sampling pipe comprises, downstream of the collecting container, a valve and a second outlet connector for withdrawing sample gas taken from the collecting container,
 the sampling pipe comprises a second pressure regulator situated between the collecting container and the second outlet connector,
 the circuit comprises a vent pipe comprising at least one pressure-sensitive relief valve, the vent pipe having a downstream discharge end opening to the outside of the device and a first upstream end connected to the sampling pipe, upstream of the collecting container, the vent pipe comprises a second upstream end connected to the sampling pipe downstream of the collecting container, the vent pipe comprises a third upstream end provided with a valve and with a nonreturn check valve, said third upstream end being connected to the sampling pipe upstream of the collecting container, the vent pipe comprises a fourth upstream end equipped with a valve and with a nonreturn check valve, said fourth upstream end being connected to the sampling pipe downstream of the collecting container, the system of valves comprises a first isolation valve arranged upstream of the first regulator, the system of valves comprises a second isolation valve arranged between the first regulator and the collecting container, the system of valves comprises a third isolation valve arranged downstream of the collecting container, the device is incorporated into a manually transportable mobile unit, the first regulator is configured to lower the pressure of the gas to a determined value between 10 bar and 100 bar, for example between 15 and 50 bar, the second regulator is configured to lower the pressure of the gas to a determined value of between 1.5 and 5 bar, and preferably between 2 and 3 bar, the collecting container comprises an internal surface that has been chemically deactivated, namely treated by a method notably of the Suifinert® type, so as to eliminate or limit the phenomena whereby reactive compounds are absorbed/decomposed.

The invention also relates to a filling station for filling hydrogen tanks, comprising a gas sampling device according to any one of the features above or below.

The invention may also relate to any alternative device or method comprising any combination of the features above or below.

BRIEF DESCRIPTION OF THE FIGURES

FIG. 1 is a schematic and partial view illustrating one example of a structure of a sampling device collaborating with a hydrogen filling station.

DETAILED DESCRIPTION OF THE INVENTION

Other specifics and advantages will become apparent on reading the following description given with reference to the single FIGURE which is a schematic and partial view illustrating one example of a structure of a sampling device collaborating with a hydrogen filling station.

The gas sampling device for a hydrogen tank filling station and depicted in the FIGURE comprises a fluid circuit 2, 3, 5 comprising a first upstream end equipped with an inlet connector 4 intended to be connected removably to an outlet connector 6 of a filling station 34.

What that means to say is that the sampling device may be connected removably directly to the downstream end of the filling station, at the gas outlet nozzle 6 intended to be connected to a tank 14 or to a vehicle 13. Alternatively, the sampling device may be connected to the outlet connector of a compressor or of a buffer storage tank of a filling station 34.

Likewise, the sampling device may be connected to the downstream outlet of a filling station, at the orifice intended to be connected usually to a hose fitted with a fuel filling gun or nozzle intended to be connected to the tanks that are to be filled. What that means to say is that the sampling device can be connected in place of a hose or upstream or downstream of a gas dispensing hose of a station.

The circuit of the sampling device comprises two pipes 2, 5, these respectively being a sampling pipe 2 and a filling pipe 5 which are connected in parallel to the inlet connector 4.

The filling pipe 5 comprises a downstream end equipped with a first outlet connector 12 intended to be connected removably to an inlet connector 35 of a tank 13, 14 that is to be filled. The filling pipe 5 is preferably without a pressure regulator or regulating valve (such members are present upstream in the circuit of the station 34). The station 34 may notably comprise its own vent circuit 42.

By contrast, the filling pipe 5 preferably comprises a safety device 37 preventing any leak in the event of the hose pulling out.

The sampling pipe 2 for its part comprises a system of valves 9, 10, 11, a first pressure regulator 7 and a collecting container 8 for collecting a sample of gas expanded by said first regulator 7.

The sampling pipe 2 comprises at least one, and preferably two, calibrated orifices arranged in series upstream of the first regulator 7, namely situated between the inlet connector 4 and the first regulator 7. More specifically, the sampling pipe 2 may comprise a first 15 and a second 16 calibrated orifice, the first calibrated orifice 15 having an orifice of dimensions greater than the dimensions of the orifice of the second calibrated orifice 16.

For example, the first calibrated orifice 15 has an orifice of dimensions of between 0.5 and 2 mm and preferably of 1 mm, while the second calibrated orifice 16 has a dimension of between 100 µm and 300 µm and preferably of 200 µm.

As illustrated, the sampling pipe 2 may comprise a first isolation valve 9 arranged upstream of the first regulator 7, between the second calibrated orifice 16 and the first regulator 7.

This first valve 9 allows the high pressure upstream circuit portion to be selectively isolated from the remainder of the circuit.

The sampling pipe 2 preferably comprises a first pressure gauge 38 arranged upstream of the first regulator 7, for example between the second calibrated orifice 16 and the first isolation valve 9.

Of course, other arrangements are possible, and for example the first isolation valve 9 may be arranged between the first calibrated orifice 15 and the second calibrated orifice 16 (as may the first pressure gauge 38).

As illustrated, the sampling pipe 2 preferably comprises a second isolation valve 10 arranged between the first regulator 7 and the collecting container 8.

In addition, an additional calibrate orifice 17 may be arranged downstream of the first regulator 7, namely between the first regulator 7 and the collecting container 8. This calibrated orifice 17 for example has an orifice of dimensions of between 200 and 900 µm, for example 500 µm.

A second pressure gauge 39 may be provided between the first regulator 7 and the collecting container 8, for example between the calibrated orifice 17 and the first regulator 7.

In the example illustrated, the sampling pipe 2 comprises, downstream of the collecting container 8, a third valve 11, a second regulator 18 (optional) and a second outlet connector 19 (preferably self-sealing) for withdrawing sample gas taken from the collecting container 8.

The second isolation valve 10 and the third isolation valve 11 allow the sample in the container 8 to be isolated at the upstream and downstream orifices thereof respectively.

As depicted, a third pressure gauge 40 may be provided downstream of the container 8 (between the container 8 and the third valve 11). A fourth pressure gauge 41 may be provided downstream of the second regulator 18.

Finally, the circuit comprises a vent pipe 3 comprising at least one pressure-sensitive relief valve 20, 22. The vent pipe 3 comprises a downstream discharge end 33 opening to the outside of the device. The vent pipe 3 comprises a first upstream end 21 connected to the sampling pipe 2, upstream of the collecting container 8 via a first pressure-sensitive relief valve 20.

The vent pipe 3 may comprise a second upstream end 23 connected to the sampling pipe 2, downstream of the collecting container 8 for example between the second outlet connector 19 and the second pressure regulator 18. The second upstream end 23 may be connected to the sampling pipe 2 via a second pressure-sensitive relief valve 22.

The vent pipe 3 may comprise a third upstream end 24 equipped with a valve 41 and with a nonreturn check valve 42 and connected to the sampling pipe 2 upstream of the collecting container 8, for example between the first regulator 7 and the third calibrated orifice 17. This valve 41 allows the circuit to be depressurized via the vent 3 at the end of use.

The vent pipe 3 may comprise a fourth upstream end 25 equipped with a valve 26 and with a nonreturn check valve 27 and connected to the sampling pipe 2 downstream of the second regulator 18. This valve 26 allows the purging of the downstream portion of the sampling circuit upstream of the second outlet connector 19.

The nonreturn check valves 27, 42 prevent any contamination of the circuit with air if the associated valves 26, 41 are opened.

The safety relief valves 20, 22 present downstream of the regulators 7, 18 allow any overpressure to be discharged to the vent 3 in the event of failure of the regulators 7, 18. For preference, the downstream end 3 of the vent forms a collector of suitable length (for example 3 meters) for discharging the flammable gas away from the users.

The vent circuit allows the purging of the filling pipe 5 (preferably a hose) that provides the connection with the tank that is to be filled. This purging can be carried out via the second end by opening the corresponding valve 41.

This avoids contaminating the tank. It will be possible for the vehicle to be used after the sample has been taken.

The calibrated orifices 15, 16 thus make it possible to limit the rate of flow of gas to the first regulator 7 and the container 8 without contaminating the gas intended to be sampled for analysis.

In addition, by limiting the downstream flow rate these calibrated orifices 15, 16 make it possible to reduce the size of the pressure-sensitive relief valves 20, 22 of the vent circuit and of the collector 3 of this vent circuit.

The third calibrated orifice 17 itself makes it possible to limit the flow rate at which the collecting container 8 is filled. This makes it possible to avoid excessive heating thereof as it fills.

The second regulator 18 arranged downstream of the container 8 allows an additional reduction in pressure, for example for distributing the sampled gas under conditions compatible with the technical features of an analyzer.

The two, sampling 2 and filling, pipes may be put into service simultaneously when the inlet connector 4 is connected to the gas outlet 6 of the filling station 34. These two lines respectively perform a filling of the tank 13, 14 of the vehicle at high pressure and a withdrawing of a sample of gas at low pressure into a container 8.

The sampling of gas for analyzing low-content impurities implies the use of suitable hardware (valves, regulators, tubes, cylinders, etc.) in terms of the technical design, cleanliness, surface treatment and surface condition.

The low pressure obtained downstream of the first regulator 7 (pressure of below 100 bar) means that suitable hardware is easy to find.

In the event that the first regulator 7 is of the controlled type, the pressure ramp and target pressure may be controlled downstream. That allows sampling at lower pressures and lower flow rates.

The hydrogen contained in the container 8 can then be analyzed in a laboratory (for example impurities can be measured for fuel cell applications).

Although of simple and inexpensive structure, the proposed solution constitutes a novel system for sampling hydrogen at the outlet of a filling station 34. Sampling can be performed simultaneously and under conditions that are identical to the filling of a tank.

The device may be interposed directly between the filling station 34 (or buffer storage tank) and the vehicle 13 using connections already present and without the need to modify the hardware.

The pressure gauges 38, 39, 40 (which are optional) indicate the pressure in the various parts of the circuit.

The sampling device may thus be incorporated into a manually transportable mobile unit 36, for example having a volume of between 0.1 and 0.3 $m^3$ and a mass of between 5 and 35 kg.

While the invention has been described in conjunction with specific embodiments thereof, it is evident that many alternatives, modifications, and variations will be apparent to those skilled in the art in light of the foregoing description. Accordingly, it is intended to embrace all such alternatives, modifications, and variations as fall within the spirit and broad scope of the appended claims. The present invention may suitably comprise, consist or consist essentially of the elements disclosed and may be practiced in the absence of an element not disclosed. Furthermore, if there is language referring to order, such as first and second, it should be understood in an exemplary sense and not in a limiting sense. For example, it can be recognized by those skilled in the art that certain steps can be combined into a single step.

The singular forms "a", "an" and "the" include plural referents, unless the context clearly dictates otherwise.

"Comprising" in a claim is an open transitional term which means the subsequently identified claim elements are a nonexclusive listing i.e. anything else may be additionally included and remain within the scope of "comprising," "Comprising" is defined herein as necessarily encompassing the more limited transitional terms "consisting essentially of" and "consisting of"; "comprising" may therefore be replaced by "consisting essentially of" or "consisting of" and remain within the expressly defined scope of "comprising".

"Providing" in a claim is defined to mean furnishing, supplying, making available, or preparing something. The step may be performed by any actor in the absence of express language in the claim to the contrary.

Optional or optionally means that the subsequently described event or circumstances may or may not occur. The description includes instances where the event or circumstance occurs and instances where it does not occur.

Ranges may be expressed herein as from about one particular value, and/or to about another particular value. When such a range is expressed, it is to be understood that another embodiment is from the one particular value and/or to the other particular value, along with all combinations within said range.

All references identified herein are each hereby incorporated by reference into this application in their entireties, as well as for the specific information for which each is cited.

What is claimed is:

1. A gas sampling device for a hydrogen tank filling station, the device comprising a circuit comprising:
   a first upstream end provided with an inlet connector intended to be connected removably to an outlet connector of a filling station:
   a sampling pipe comprising a system of valves, a first pressure regulator and a container for collecting a sample of gas expanded by said first regulator;
   a filling pipe comprising a downstream end provided with a first outlet connector intended to be connected removably to an inlet connector of a tank that is to be filled, wherein the sampling pipe and the filling pipe are connected in parallel to the inlet connector of the first upstream end of the circuit; and
   a vent pipe comprising at least one pressure-sensitive relief valve, the vent pipe having a downstream discharge end opening to the outside of the device, a first upstream end connected to the sampling pipe upstream of the collecting container, and a second upstream end connected to the sampling pipe downstream of the collecting container.

2. The device of claim 1, wherein the sampling pipe further comprises at least one calibrated orifice situated upstream of the first pressure regulator between the inlet connector and the first pressure regulator.

3. The device of claim 1, wherein the sampling pipe further comprises a calibrated orifice situated downstream of the first regulator between the first regulator and the collecting container.

4. The device of claim 1, wherein the sampling pipe further comprises first and second calibrated orifices arranged in series upstream of the first regulator between the inlet connector and the first regulator, the first calibrated orifice having dimensions greater than that of the second calibrated orifice.

5. The device of claim 1, wherein the sampling pipe further comprises, downstream of the collecting container, a valve and a second outlet connector for withdrawing sample gas taken from the collecting container.

6. The device of claim 5, wherein the sampling pipe further comprises a second pressure regulator situated between the collecting container and the second outlet connector.

7. The device of claim 1, wherein a first isolation valve is disposed upstream of the first regulator.

8. The device of claim 7, wherein a second isolation valve is disposed between the first regulator and the collecting container.

9. The device of claim 8, wherein a third isolation valve is disposed downstream of the collecting container.

10. The device of claim 1, wherein it is arranged and configured to be a manually transportable.

11. A filling station for filling hydrogen tanks, comprising a gas sampling device of claim 1.

* * * * *